US007915225B2

(12) United States Patent
Finck

(10) Patent No.: US 7,915,225 B2
(45) Date of Patent: *Mar. 29, 2011

(54) SOLUBLE TUMOR NECROSIS FACTOR RECEPTOR TREATMENT OF MEDICAL DISORDERS

(75) Inventor: Barbara K Finck, Mercer Island, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/394,962

(22) Filed: Feb. 27, 2009

(65) Prior Publication Data

US 2009/0163424 A1    Jun. 25, 2009

Related U.S. Application Data

(60) Division of application No. 10/853,479, filed on May 25, 2004, now abandoned, which is a division of application No. 09/602,351, filed on Jun. 23, 2000, now abandoned, and a continuation-in-part of application No. 09/373,828, filed on Aug. 13, 1999, now abandoned.

(60) Provisional application No. 60/164,676, filed on Nov. 10, 1999, provisional application No. 60/184,864, filed on Feb. 25, 2000, provisional application No. 60/130,074, filed on Apr. 19, 1999, provisional application No. 60/134,320, filed on May 14, 1999, provisional application No. 60/143,959, filed on Jul. 15, 1999, provisional application No. 60/148,234, filed on Aug. 11, 1999.

(51) Int. Cl.
*A61K 38/16* (2006.01)
*C07K 14/715* (2006.01)
*C07K 14/525* (2006.01)

(52) U.S. Cl. ...... 514/21.2; 514/18.7; 514/169; 514/863; 552/588; 607/94; 530/350; 530/866

(58) Field of Classification Search ........................ None
See application file for complete search history.

(56) References Cited

U.S. PATENT DOCUMENTS

| | | |
|---|---|---|
| 4,006,224 A | 2/1977 | Prudden |
| 4,965,271 A | 10/1990 | Mandrell et al. |
| 5,096,906 A | 3/1992 | Mandrell et al. |
| 5,196,430 A | 3/1993 | Mandrell et al. |
| 5,342,613 A | 8/1994 | Creaven et al. |
| 5,344,915 A | 9/1994 | LeMaire et al. |
| 5,420,154 A | 5/1995 | Christensen et al. |
| 5,447,851 A | 9/1995 | Beutler et al. |
| 5,508,300 A | 4/1996 | Duplantier |
| 5,541,219 A | 7/1996 | Fenton et al. |
| 5,545,614 A | 8/1996 | Stamler et al. |
| 5,563,143 A | 10/1996 | Cohan et al. |
| 5,596,013 A | 1/1997 | Duplantier |
| 5,605,690 A | 2/1997 | Jacobs et al. |
| 5,610,279 A | 3/1997 | Brockhaus et al. |
| 5,629,285 A | 5/1997 | Black et al. |
| 5,641,814 A * | 6/1997 | Martin ........................ 514/724 |
| 5,656,272 A | 8/1997 | Le et al. |
| 5,658,581 A | 8/1997 | De Lacharriere et al. |
| 5,691,382 A | 11/1997 | Crimmin et al. |
| 5,698,195 A | 12/1997 | Le et al. |
| 5,700,838 A | 12/1997 | Dickens et al. |
| 5,714,146 A | 2/1998 | Lewis et al. |
| 5,747,514 A | 5/1998 | Beckett et al. |
| 5,756,449 A | 5/1998 | Andersen et al. |
| 5,767,065 A | 6/1998 | Mosley et al. |
| 5,795,859 A | 8/1998 | Rathjen et al. |
| 5,821,262 A | 10/1998 | Crimmin et al. |
| 5,834,485 A | 11/1998 | Dyke et al. |
| 5,869,511 A | 2/1999 | Cohan et al. |
| 5,872,146 A | 2/1999 | Baxter et al. |
| 5,888,511 A | 3/1999 | Skurkovich et al. |
| 5,902,827 A | 5/1999 | Pamukcu et al. |
| 5,919,452 A | 7/1999 | Le et al. |
| 5,958,413 A | 9/1999 | Anagnostopulos et al. |
| 5,993,833 A | 11/1999 | De Lacharriere et al. |
| 5,994,510 A | 11/1999 | Adair et al. |
| 6,015,557 A | 1/2000 | Tobinick et al. |
| 6,020,323 A | 2/2000 | Cohen et al. |
| 6,083,534 A | 7/2000 | Wallach et al. |
| 6,107,349 A * | 8/2000 | Mantynen ................. 424/776 |
| 6,117,895 A * | 9/2000 | Wachtel et al. .............. 514/376 |
| 6,143,730 A | 11/2000 | Parish et al. |
| 6,143,866 A | 11/2000 | Brewer et al. |
| 6,177,077 B1 | 1/2001 | Tobinick |
| 6,221,675 B1 | 4/2001 | Hauptmann et al. |
| 6,277,387 B1 | 8/2001 | De Lacharriere et al. |
| 6,277,969 B1 | 8/2001 | Le et al. |
| 6,284,471 B1 | 9/2001 | Le et al. |
| 6,300,349 B1 | 10/2001 | Margolin |
| 6,306,820 B1 | 10/2001 | Bendele et al. |
| 6,313,269 B1 | 11/2001 | Deen et al. |
| 6,379,666 B1 | 4/2002 | Tobinick |
| 6,419,934 B1 | 7/2002 | Tobinick |
| 6,495,604 B1 | 12/2002 | Ichimori et al. |
| 6,498,237 B2 | 12/2002 | Rathjen et al. |
| 6,537,540 B1 | 3/2003 | Burstein et al. |
| 6,537,549 B2 | 3/2003 | Tobinick |

(Continued)

FOREIGN PATENT DOCUMENTS

EP    0 308 378 B2    3/1989

(Continued)

OTHER PUBLICATIONS

Abu-Shakra, M., et al., "Longterm methotrexate therapy in psoriatic arthritis: clinical and radiological outcome," J Rheumatol 22:241-245, 1995.

(Continued)

*Primary Examiner* — David S Romeo
(74) *Attorney, Agent, or Firm* — Rosemary Sweeney

(57) ABSTRACT

The invention pertains to methods and compositions for treating medical disorders characterized by elevated levels or abnormal expression of TNFα by administering a TNFα antagonist, such as recombinant TNFR:Fc.

20 Claims, No Drawings

U.S. PATENT DOCUMENTS

| | | | |
|---|---|---|---|
| 6,572,852 | B2 | 6/2003 | Smith |
| 6,673,908 | B1 | 1/2004 | Stanton, Jr. |
| 6,989,147 | B2 | 1/2006 | Fisher et al. |
| 7,122,183 | B2 * | 10/2006 | Mohler et al. ............. 424/133.1 |
| 7,253,264 | B1 | 8/2007 | Lauffer et al. |
| 7,335,358 | B2 | 2/2008 | Le et al. |
| 2002/0012962 | A1 | 1/2002 | Stahl et al. |
| 2002/0022720 | A1 | 2/2002 | Le et al. |
| 2002/0183485 | A1 | 12/2002 | Hauptmann et al. |
| 2003/0012786 | A1 | 1/2003 | Teoh et al. |
| 2003/0054439 | A1 | 3/2003 | Fisher et al. |
| 2003/0086925 | A1 | 5/2003 | Skurkovich et al. |
| 2003/0103942 | A1 | 6/2003 | Burstein et al. |
| 2003/0113318 | A1 | 6/2003 | Tobinick |
| 2003/0143603 | A1 | 7/2003 | Giles-Komar et al. |

FOREIGN PATENT DOCUMENTS

| | | |
|---|---|---|
| EP | 0 325 471 A1 | 7/1989 |
| EP | 0 393 438 B1 | 10/1990 |
| EP | 0 398 327 B1 | 11/1990 |
| EP | 0 422 339 B1 | 4/1991 |
| EP | 0 516 785 B1 | 12/1992 |
| EP | 0 567 566 B2 | 11/1993 |
| EP | 0 639 079 B1 | 11/1993 |
| EP | 0 377 823 B1 | 7/1994 |
| EP | 0 626 389 A1 | 11/1994 |
| EP | GB 2291422 A | 1/1996 |
| EP | 0 839 046 B1 | 5/1998 |
| EP | 0 869 179 A1 | 10/1998 |
| EP | 0 870 827 A2 | 10/1998 |
| EP | 0 927 758 A2 | 7/1999 |
| EP | 0 958 820 A1 | 11/1999 |
| EP | 0 610 201 B1 | 5/2001 |
| EP | 1 097 945 A2 | 5/2001 |
| EP | 1 170 017 A1 | 9/2002 |
| WO | WO 92/01472 | 2/1992 |
| WO | WO 92/13095 A1 | 8/1992 |
| WO | WO 92/16221 A1 | 10/1992 |
| WO | WO 92/16553 A1 | 10/1992 |
| WO | WO 95/06031 | 3/1995 |
| WO | WO 95/20402 | 8/1995 |
| WO | WO 95/34326 A1 | 12/1995 |
| WO | WO 95/35283 | 12/1995 |
| WO | WO 95/35285 | 12/1995 |
| WO | WO 96/00215 | 1/1996 |
| WO | WO 96/01825 | 1/1996 |
| WO | WO 96/04388 | 2/1996 |
| WO | WO 97/29131 A1 | 8/1997 |
| WO | WO 97/41895 A2 | 11/1997 |
| WO | WO 98/01555 | 1/1998 |
| WO | WO 98/05357 | 2/1998 |
| WO | WO 98/17799 | 4/1998 |
| WO | WO 98/24463 | 6/1998 |
| WO | WO 98/24463 | 8/1998 |
| WO | WO 98/46642 | 10/1998 |
| WO | WO 98/51344 | 11/1998 |
| WO | WO 98/54201 A1 | 12/1998 |
| WO | WO 99/15524 | 4/1999 |
| WO | WO 99/18095 | 4/1999 |
| WO | WO 99/31128 | 6/1999 |
| WO | WO 99/31128 A2 | 6/1999 |
| WO | WO 99/46242 | 9/1999 |
| WO | WO 00/67790 A1 | 11/2000 |
| WO | WO 00/73481 A1 | 12/2000 |
| WO | WO 01/00229 A1 | 1/2001 |
| WO | WO 01/37874 | 5/2001 |

OTHER PUBLICATIONS

Alonso, J.C., et al., "Psoriatic arthritis (PA): a clinical, immunological and radiological study of 180 patients," Br J Rheumatol 30:245-250, 1991.

Ameglio, F., et al., "Interleukin-6 and tumour necrosis factor levels decrease in the suction blister fluids of psoriatic patients during effective therapy," Dermatology 189:359-363, 1994.

Antoni C. et al., "Successful treatment of severe psoriatic arthritis with infliximab," Arthritis & Rheumatism, vol. 42, p. S371, Sep. 1999, Abstract 1801.

Arias, A, et al., "Tumor necrosis factor-alpha gene polymorphism in psoriasis," Exp Clin Immunogenet 14:118-122, 1997.

Austin, L., et al., "Intracellular TNF-$\alpha$, IFN-$\gamma$, and IL-2 identify TC1 and TH1 effector populations in psoriasis vulgaris plaque lymphocytes: single-cell analysis by flow cytometry," J Dermatol Sci 16 (Suppl. 1), Mar. 1998.

Austin, L., et al., "Intracellular TNF-$\alpha$, IFN-$\gamma$, and IL-2 identify TC1 and TH1 effector populations in psoriasis vulgaris plaque lymphocytes: single-cell analysis by flow cytometry," J Invest Dermatol 1101 #4, Apr. 1998.

Barker, JNWN et al., "Marked synergism between tumor necrosis factor-$\alpha$ and interferon-$\gamma$ in regulation of keratinocyte-derived adhesion molecules and chemotactic factors," J Clin Invest 85:605-608, 1990.

Barnes et al., "Nuclear factor-kappaB: a pivotal transcription factor in chronic inflammatory diseases," N Engl J Med 336(15):1066-1071, 1997.

Baum et al., "Treatment of psoriatic arthritis with 6-mercaptopurine," Arthritis and Rheum., 16(2):139-147 (1973).

Bonifati, C., et al., "Correlated increases of tumour necrosis factor-$\alpha$, interleukin-6 and granulocyte monocyte-colony stimulating factor levels in suction blister fluids and sera of psoriatic patients—relationships with disease severity," Clin Exp Dermatol 19:383-387, 1994.

Bonifati, C., et al., Soluble E-selectin and soluble tumour necrosis factor receptor (60kD) serum levels in patients with psoriasis, Dermatology 190:128-131, 1995.

Breathnach, S.M., "Spondyloarthropathies: psoriatic arthritis: etiology and pathogenesis," in Rheumatology, Mosby, London, John H. Klippel & Paul A. Dieppe, eds., 2d ed., 1998, pp. 22.1-22.4.

Brockbank and Gladman, "Diagnosis and management of psoriatric arthritis," Drugs 62(17):2447-2457, 2002.

Bundow et al., "Etanercept: a treatmentoption for human immunodeficiency virus (HIV)-related psoriatic arthropathy," Blood 94(Suppl):47b (1999), Abstract 3361.

Centola, G.M., et al., "Differential responses of human sperm to varying concentrations of pentoxyfylline with demonstration of toxicity," J Androl 16(2):136-142, 1995.

Chodorowska, G., "Plasma concentrations of IFN-$\gamma$ and TNF-$\alpha$ in psoriatic patients before and after local treatment with dithranol ointment," J Eur Acad Dermatol Venereol 10:147-151, 1998.

Clegg, D.O., et al., "Comparison of sulfasalazine and placebo in the treatment of psoriatic arthritis," Arthritis Rheum 39(12):2013-2020, 1996.

Cosman, D., "The tumor-necrosis-factor-related superfamily of ligands and receptors," in Blood Cell Biochemistry vol. 7: Hematopoietic Cell Growth Factors and Their Receptors, Plenum Press, New York, A.D. Whetton & J. Gordon, eds., 1996, pp. 51-77.

Creaven, P.J. and Stoll, Jr., H.L., "Response to tumor necrosis factor in two cases of psoriasis," J Am Acad Dermatol 24:735-737, 1991.

de Rie, M. A. et al., "Low-dose narrow-band UVB phototherapy combined with topical therapy is effective in psoriasis and does not inhibit systemic T-cell activation," Dermatology 196:412-417, 1998.

Debets, R., et al., "Expression of cytokines and their receptors by psoriatic fibroblasts. II. Decreased TNF receptor expression," Cytokine 8(1):80-88, 1996.

Dembic et al., "Two human TNF receptors have similar extracellular, but distinct intracellular, domain sequences," Cytokine 2(4):231-237, 1990.

Dobmeyer, J.M., et al., "Importance of HLA-DR+ and CD1a+ epidermal cells for cytokine production in psoriasis," Adv Exp Med Biol 378:539-541, 1995.

Dorwart, B.B., et al., "Chrysotherapy in psoriatic arthritis," Arthritis Rheum 21(5):513-515, 1978.

Dunky, A., et al., "Interactions of lymphocytes from patients with psoriatic arthritis or healthy controls and cultured endothelial cells," Clin Immunol Immunopathol 85(3):297-314, 1997.

Elferink, J.G.R., et al., "The effect of pentoxifylline on human neutrophil migration: a possible role for cyclic nucleotides," Biochem Pharmacol 54:475-480, 1997.

Espinoza et al., "Psoriatic arthritis: clinical response and side effects to methotrexate therapy," J Rheumatol 19:872-877, 1992.

Ettehadi, P., et al., "Elevated tumour necrosis factor-alpha (TNF-α) biological activity in psoriatic skin lesions," Clin Exp Immunol 96:146-151, 1994.

Feldman et al., "Anti-TNF alpha therapy is useful in rheumatoid arthritis and Crohn's disease: analysis of the mechanism of action predicts utility in other diseases," Transplant Proc 30(8):4126-4127, 1998.

Fernandez-Real et al., "Tumor necrosis factor system activity is associated with insulin resistance and dislipidemia in myotonic dystrophy," Diabetes 48:1108-1112, 1999.

Fisher, Jr. et al., "Treatment of septic shock with the tumor necrosis factor receptor:Fc fusion protein," N Engl J Med 334:1697-1702, 1996.

Fukuoka, M., et al., "RANTES expression in psoriatic skin, and regulation of RANTES and IL-8 production in cultured epidermal keratinocytes by active vitamin $D_3$ (tacalcitol)," Br J Dermatol 138:63-70, 1998.

Furst et al., "Building towards a consensus for the use of tumor necrosis factor blocking agents," Ann Rheum Dis 58:725-726, 1999.

Gilhar, A., et al., "In vivo effects of cytokines on psoriatic skin grafted on nude mice: involvement of the tumour necrosis factor (TNF) receptor," Clin Exp Immunol 106:134-142, 1996.

Gladman, D.D., "Psoriatic arthritis: recent advances in pathogenesis and treatment," Rheum Dis Clin North Am 18(1):247-256, 1992.

Gladman, D.D., et al., "Longitundinal study of clinical and radiological progression in psoriatic arthritis," J Rheumatol 17:809-812, 1990.

Gladman, D.D., et al., "Psoriatic arthritis (PSA)—an analysis of 220 patients," Quarterly Journal of Medicine, New Series 62, 238:127-141, 1987.

Gosselin and Martinez, "Impact of TNF-a blockade on TGF-beta1 and type I collagen mRNA expression in dystrophic muscle," Muscle Nerve 30(2):244-246, 2004.

Griffiths, C.E.M., et al., "Elevated levels of circulating intercellular adhesion molecule-3 (cICAM-3) in psoriasis," Acta Derm Venereol (Stockh) 76:2-5, 1996.

Griffiths, CEM et al., "Modulation of leucocyte adhesion molecules, a T-cell chemotaxin (IL-8) and a regulatory cytokine (TNF-α) in allergic contact dermatitis (rhus dermatitis)," Br J Dermatol 124:519-526, 1991.

Groves, RW et al., "Tumour necrosis factor alpha is pro-inflammatory in normal human skin and modulates cutaneous adhesion molecule expression," Br J Dermatol 132:345-352, 1995.

Gruss and Dower, "The TNF ligand superfamily and its relevance for human diseases," Cytokines Cell Mol Ther 1:75-105, 1995.

Heilig et al., "The tumor necrosis factor system in rheumatic diseases," Arthritis & Rheumatism, Abstracts of Scientific Presentations, Annual Scientific Meeting of the American College of Rheumatology, 35(Suppl.9):5174, Sep. 1992.

Heilig et al., "Expression von TNF-Rezeptoren bei rheumatoider arthritis und spondarthropathien," Z Rheum 52:383-389, 1993, with English Abstract.

Helliwell, P.S. and Wright, V., "Spondyloarthropathies: psoriatic arthritis: clinical features," in Rheumatology, Mosby, London, John H. Klippel & Paul A. Dieppe, eds., 2d ed., 1998, pp. 21.1-21.8.

Hodgetts et al., "Reduced necrosis of dystrophic muscle by depletion of host neutrophils, or blocking TNFalpha function with etanercept in mdx mice," Neuromuscul Disord 16(9-10):591-602, 2006.

Höhler, T., et al., "A TNF-α promoter polymorphism is associated with juvenile onset psoriasis and psoriatic arthritis," J Invest Dermatol 109:562-565, 1997.

Jones, G., et al., "Psoriatic arthritis: a quantitative overview of therapeutic options," Br J Rheumatol 36:95-99, 1997.

Kapp, A., et al., "Immunomodulating cytokines in atopic dermatitis and psoriasis: production of tumour necrosis factor and lymphotoxin by mononuclear cells in vitro," Br J Dermatol 122:587-592, 1990.

Kristensen, M., et al., "Localization of tumour necrosis factor-alpha (TNF-α) and its receptors in normal and psoriatic skin: epidermal cells express the 55-kD but not the 75-kD TNF receptor," Clin Exp Immunol 94:354-362, 1993.

Lechner et al., "A recombinant tumor necrosis factor-α p80 receptor:Fc fusion protein decreases circulating bioactive tumor necrosis factor-α but not lung injury or mortality during immunosuppression-related gram-negative bacteremia," J Crit Care 12(1):28-38, 1997.

Linden, KG and Weinstein, GD, "Psoriasis: current perspectives with an emphasis on treatment," Am J Med 107:595-605, 1999.

Lipsky et al., "Outcome of specific COX-2 inhibition in rheumatoid arthritis," J Rheumatol 24(Suppl.49):9-14, 1997.

Löntz, W., et al., "Increased mRNA expression of manganese superoxide dismutase in psoriasis skin lesions and in cultured human keratinocytes exposed to IL-1β and TNF-α," Free Radic Biol Med 18(2):349-355, 1995.

Mace K. et al., "Pharmacodynamics of cA2: implications for immunotherapy," European Cytokine Network, 7(2):308, Apr. 1996, Abstract 245.

Malkani, A.K., et al., "Normal response to tumor necrosis factor-alpha and transforming growth factor-beta by keratinocytes in psoriasis," Exp Dermatol 2:224-230, 1993.

Markusheva, L.I., et al., "Serum tumor necrosis factor (alpha) in psoriasis," Vefnik Dermatology 0/3:8-11, 1997.

Mease, P. et al., "ENBREL® (etanercept) in patients with psoriatic arthritis and psoriasis," Arthritis Rheum 42 (9 Suppl):5377, 1999.

Mease, P. et al., "(ETANERCEPT) in patients with psoriatic arthritis and psoriasis," Immunex Corporation, Abstract No. 1835, Sep. 1999.

Mease, P.J. et al., "Etanercept in the treatment of psoriatic arthritis and psoriasis: a randomised trial," Lancet 356:385-390, 2000.

Mizutani, H., et al., "Role of increased production of monocytes TNF-α, IL-1β and IL-6 in psoriasis: relation to focal infection, disease activity and responses to treatments," J Dermatol Sci 14:145-153, 1997.

Mohler K.M. et al., "Soluble tumor necrosis factor (TNF) receptors are effective therapeutic agents in lethal endotoxemia and function simultaneously as both TNF carriers and TNF antagonists," J Immunol 151:1548-1561, 1993.

Moreland et al., "Treatment of rheumatoid arthritis with a recombinant human tumor necrosis factor receptor (p75)-Fc fusion protein," N Engl J Med 337(3):141-147, 1997.

Mussi, A., et al., "Serum TNF-alpha levels correlate with disease severity and are reduced by effective therapy in plaque-type psoriasis," J Biol Regul Homeost Agents 11:115-118, 1997.

Nickoloff, B.J., "Pathogenesis and immunointervention strategies for psoriasis," Mol Med Today, 512-513, 1998.

Nickoloff, B.J., "The cytokine network in psoriasis," Acta Dermatol 127:871-884, 1991.

Nickoloff, B.J., et al., "Cellular localization of interleukin-8 and its inducer, tumor necrosis factor-alpha in psoriasis," Am J Pathol 138(1):129-140, 1991.

Okubo, Y. and Koga, M., "Peripheral blood monocytes in psoriatic patients overproduce cytokines," J Dermatol Sci 17:223-232, 1998.

Omulecki, A., et al., "Is pentoxifylline effective in the treatment of psoriasis?" J Am Acad Dermatol 34(4):714-715, 1996.

Oxholm, A., "Epidermal expression of interleukin-6 and tumour necrosis factor-alpha in normal and immunoinflammatory skin states in humans," APMIS 100 (Suppl. 24):5-32, 1992.

Partsch, G, et al., "Upregulation of cytokine receptors sTNF-R55, sTNF-R75, and sIL-2R in psoriatic arthritis synovial fluid," J. Rheumatol 25:105-110, 1998.

Partsch, G., et al., "Highly increased levels of tumor necrosis factor-α and other proinflammatory cytokines in psoriatic arthritis synovial fluid," J Rheumatol 24:518-523, 1997.

Partsch, G., et al., "T cell derived cytokines in psoriatic arthritis synovial fluids," Ann Rheum Dis 57:691-693, 1998.

Pennica et al., "Human tumour necrosis factor: precursor structure, expression and homology to lymphotoxin," Nature 312(20/27):724-729, 1984.

Pierno et al., "Role of tumour necrosis factor a, but not of cyclo-oxygenase-2-derived eicosanoids, on functional and morphological indices of dystrophic progression in mdx mice: a pharmacological approach," Neuropathol Appl Neurobiol 33(3):344-359, 2007.

Pigatto, P.D., et al., "Factors secreted by untreated psoriatic monocytes enhance neutrophil functions," J Invest Dermatol 94:372-376, 1990.

Porreca et al., "Haemostatic abnormalities, cardiac involvement and serum tumor necrosis factor levels in X-linked dystrophic patients," Thromb Haemost 81(4):543-546, 1999.

Reichrath, J., et al., "Topical calcitriol (1,25-Dihydroxyvitamin $D_3$) treatment of psoriasis: an immunohistological evaluation," Acta Derm Venereol (Stockh) 77:268-272, 1997.

Ritchlin, C., et al., "Patterns of cytokine production in psoriatic synovium," J Rheumatol 25:1544-1552, 1998.

Sagawa, Y., et al., "Is sustained production of tumor necrosis factor-α relevant to the development of pustular psoriasis?" Dermatology 187:81-83, 1993.

Salvarani, C., et al., "Psoriatic arthritis," Curr Opin Rheumatol 10:299-305, 1998.

Sandborn et al., "Etanercept for active Crohn's disease: a randomized, double-blind, placebo-controlled trial," Gastroenterology 121:1088-1094, 2001.

Seishima, M., et al., "Increased serum soluble Fas, tumor necrosis factor α and interleukin 6 concentrations in generalized pustular psoriasis," Dermatology 196:371-372, 1998.

Shiohara, T., et al., "Differential effects of cyclosporine and etretinate on serum cytokine levels in patients with psoriasis," J Am Acad Dermatol 27:568-574, 1992.

Smith et al., "A receptor for tumor necrosis factor defines an unusual family of cellular and viral proteins," Science 248:1019-1023, 1990.

Takematsu et al., "Absence of tumor necrosis factor-α in suction blister fluids and stratum corneum from patients with psoriasis," Arch Dermatol Res 281:398-400, 1989.

Takematsu, H., et al., "Systemic TNF administration in psoriatic patients: a promising therapeutic modality for severe psoriasis," Br J Dermatol 124:209-210, 1991.

Terajima, S., et al., "An important role of tumor necrosis factor-α in the induction of adhesion molecules in psoriasis," Arch Dermatol Res 290:246-252, 1998.

Tigalonova, M., et al., "Serum levels of interferons and TNF-α are not correlated to psoriasis activity and therapy," Acta Derm Venereol (Stockh) Suppl. 186:25-27, 1994.

van der Poll et al., "Pretreatment with a 55-kDa tumor necrosis factor receptor-immunoglobulin fusion protein attenuates activation of coagulation, but not of fibrinolysis, during lethal bacteremia in baboons," J Infect Dis. 176(1):296-299, 1997.

van der Poll and van Deventer, "Cytokines and anticytokines in the pathogenesis of sepsis," Infect Dis Clin North Am 13(2):413-426, 1999.

Veale, D., et al., "Reduced synovial membrane macrophage numbers, ELAM-1 expression, and lining layer hyperplasia in psoriatic arthritis as compared with rheumatoid arthritis," Arthritis Rheum 36(7):893-900, 1993.

Weinblatt, M.E., et al., "A trial of Etanercept, a recombinant tumor necrosis factor receptor:Fc fusion protein, in patients with rheumatoid arthritis receiving methotrexate," N Engl J Med 340:253-259, 1999.

Willkens, R.F., et al., "Randomized, double-blind, placebo controlled trial of low-dose pulse methotrexate in psoriatic arthritis," Arthritis Rheum 27(4):376-381, 1984.

Yazici, Y. et al., "Etanercept in the treatment of severe, resistant psoriatic arthritis," Arthritis Rheum 42(Suppl.):5379, 1999.

National Psoriasis Foundation, Psoriatic Arthritis Fact Sheet, "Psoriatic Arthritis Description and Photos," www.psoriasis.org/psortypes/arthritis.html, pp. 1-3, printed Jul. 21, 1999.

National Psoriasis Foundation, "Scientifically Proven Treatments for Psoriasis," www.psoriasis.org/treatsci.html, pp. 1-10, printed Jul. 21, 1999.

Office Action (Paper No. 12), U.S. Appl. No. 09/373,828, mailed Mar. 16, 2001.

Office Action (Paper No. 13), U.S. Appl. No. 09/602,351, mailed Apr. 22, 2002.

Office Action (Paper No. 20), U.S. Appl. No. 09/602,351, mailed May 5, 2003.

Ackermann et al., "Mast cells of psoriatic and atopic dermatitis skin are positive for TNF-α and their degranulation is associated with expression of ICAM-1 in the epidermis," Arch Dermatol Res 290:353-359, 1998.

Asadullah et al., "IL-10 is a Key Cytokine in Psoriasis," J Clin Invest 101(4): 783-794, 1998.

Bédard et al., "Release of Interleukin-8, Interleukin-6, and Colony-stimulating Factors by Upper Airway Epithelial Cells: Implications for Cystic Fibrosis," Am J Respir Cell Mol Biol 9:455-462, 1993.

Boehncke et al., "The SCID-hu xenogeneic transplantation model allows screening of anti-psoriatic drugs," Arch Dermatol Res 291:104-106, 1999.

Boehncke, "The SCID-hu xenogeneic transplantation model: complex but telling," Arch Dermatol Res 291:367-373, 1999.

Boehncke et al., "Animal models of psoriasis," Clinics in Dermatology 25:596-605, 2007.

Boetticher et al., "Clinical—Liver, Pancreas, and Biliary Tract, A Randomized, Double-Blinded, Placebo-Controlled Multicenter Trial of Etanercept in the Treatment of Alcoholic Hepatitis," Gastroenterology 135:1953-1960, 2008.

Cannon et al., "Circulating Interleukin-1 and Tumor Necrosis Factor in Septic Shock and Experimental Endotoxin Fever," J Infect Dis 161:79-84, 1990.

Caproni et al., "The role of lymphocytes, granulocytes, mast cells and their related cytokines in lesional skin of linear IgA bullous dermatosis," Br J Dermatol 140:1072-1078, 1999.

Chi et al. "Linear IgA Bullous Dermatosis Associated with Ulcerative Colitis," J Dermatol 26:150-153, 1999.

Cox, "Glucocorticoid Treatment Inhibits Apoptosis in Human Neutrophils," J Immunol 154:4719-4725, 1995.

Gearing et al. "Cytokines in Skin Lesions of Psoriasis," Cytokine 2(1):68-75, 1990.

Hatae et al., "The effect of rolipram on the production of cytokines in HTLV-I infected cell lines and peripheral blood mononuclear cells of patients with HTLV-I-associated myelopathy (HAM)," J Neurol Sci 148:87-94, 1997.

Johansen et al. "Vaccination Promotes TH1-like Inflammation and Survival in Chronic Pseudomonas aeruginosa Pneumonia. A new Prophylactic Principle," Behring Inst Mitt 98:269-273, 1997.

Knutsen et al., "Allergic Bronchopulmonary Mycosis Complicating Cystic Fibrosis," Seminars in Respiratory Infections 7(3):179-192, 1992.

Kobayashi et al., "A Case of Linear IgA Disease: An Immunofluorescent Study Using Confocal Laser Scan Microscopy," J Dermatol 24:306-309, 1997.

Menter et al., "Guidelines of care for the management of psoriasis and psoriatic arthritis," J Am Acad Dermatol 58:826-850, 2008.

Moser et al., "Chronic Pseudomonas aeruginosa lung infection is more severe in $Th_2$ responding BALB/c mice compared to $Th_1$ responding C3H/HeN mice," APMIS 105:838-842, 1997.

Moser et al., "The immune response to chronic Pseudomonas aeruginosa lung infection in cystic fibrosis patients is predominantly of the Th2 type." APMIS 108:329-335, 2000.

Nagano et al., "Effect of tumour necrosis factor in the mouse-tail model of psoriasis," Arch Dermatol Res 282:459-462, 1990.

Nittoh et al., "Effects of glucocorticoids on apoptosis of infiltrated eosinophils and neutrophils in rats," Eur J Pharmacol 354:73-81, 1998.

Olaniran et al., "Cytokine expression in psoriatic skin lesions during PUVA therapy," Arch Dermatol Res 288:421-425, 1996.

Oxholm et al., "Expression of Interleukin-6-like Molecules and Tumour Necrosis Factor after Topical Treatment of Psoriasis with a New Vitamin D Analogue (MC 903)," Acta Derm Venereol (Stockh) 69:385-390, 1989.

Partsch et al., "T cell derived cytokines in psoriatic arthritis synovial fluids," Ann Rheum Dis 57:691-693, 1998.

Taylor, "Pathogenesis and treatment of HTLV-I associated myelopathy," Sex Transm Inf 74:316-322, 1998.

Tigalonowa et al., "Immunological Changes Following Treatment of Psoriasis with Cyclosporin," Acta Derm Venereol (Stockh) 146:142-146, 1989.

Wrone-Smith et al., "Dermal Injection of Immunocytes Induces Psoriasis," J Clin Invest 98(8):1878-1887, 1996.

Abraham et al., "Efficacy and safety of monoclonal antibody to human tumor necrosis factor α in patients with sepsis syndrome" (1995), JAMA 273: 934-941.

Dubost et al., "An open study of the anti-TNF alpha agent pentoxifylline in the treatment of rheumatoid arthritis" (1997), Rev. Rhum. [Engl. Ed.] 64(12): 789-793.

Fisher et al., "Treatment of septic shock with the tumor necrosis factor receptor:Fc fusion protein" (1996), N. Engl. J. Med. 334(26): 1697-1702.

Girardin et al., "Imbalance between tumour necrosis factor-alpha and soluble TNF receptor concentrations in severe meningococcaemia" (1992), Immunology 76: 20-23.

Immunex Corporation, SEC Filing 10-K405, 10-K, Filing 96535614 (Dec. 31, 1995).

The Lenercept Multiple Sclerosis Study Group and the University of British Columbia MS/MRI Analysis Group, "TNF neutralization in MS. Results of a randomized, placebo-controlled multicenter study" (1999), Neurology 53: 457-465.

MacDonald et al., "Tumour necrosis factor-alpha and interferon-gamma production measured at the single cell level in mormal and inflamed human intestine" (1990), Clin. Exp. Immunol. 81: 301-305.

Marano et al., "Serum cachectin/tumor necrosis factor in critically ill patients with burns correlates with infection and mortality" (1990), Surg. Gynecol. Obstet. 170: 32-38.

Mohler et al., "Soluble tumor necrosis factor (TNF) receptors are effective therapeutic agents in lethal endotoxemia and function simultaneously as both TNF carriers and TNF antagonists" (1993), J. Immunol. 151: 1548-1561.

Noseworthy et al., "The Mayo Clinic-Canadian cooperative trial of sulfasalazine in active multiple sclerosis" (1998), Neurology 51: 1342-1352.

Sandborn et al., "Etanercept for active Crohn's disease: a randomized double-blind, placebo-controlled trial" (2001), Gastroenterology 121(5): 1088-1094.

Sastry, "Inhibition of TNF-$\alpha$ synthesis with thalidomide for prevention of acute exacerbations and altering the natural history of multiple sclerosis" (1999), Med. Hypotheses 53(1): 76-77.

Schmidt et al., "Thalidomide inhibits TNF response and increases survival following endotoxin injection in rats" (1996), J. Surg. Res. 63(1): 143-146.

Sharief et al., "Association between tumor necrosis factor-$\alpha$ and disease progression in patients with multiple sclerosis" (1991), New Engl. J. Med. 325(7): 467-472.

Silva et al., "Prophylactic and therapeutic effects of a monoclonal antibody to tumor necrosis factor-$\alpha$ in experimental gram-negative shock" (1990), J. Infect. Dis. 162: 421-427.

Sommer et al., "The antidepressant rolipram suppresses cytokine production and prevents autoimmune encephalomyelitis" (1995), Nat. Med. 1(3): 244-248.

Targan et al., "A short-term study of chimeric monoclonal antibody cA2 to tumor necrosis factor $\alpha$ for Crohn's disease" (1997), N. Engl. J. Med. 337: 1029-1035.

Tracey et al., "Anti-cachectin/TNF monoclonal antibodies prevent septic shock during lethal bacteraemia" (1987), Nature 330: 662-664.

Tremaine, "The medical treatment of active Crohn's disease" (1999), Drugs Today 35 (Suppl. A): 89-96.

van Oosten et al., "Increased MRI activity and immune activation in two multiple sclerosis patients treated with the monoclonal anti-tumor necrosis factor antibody cA2" (1996), Neurology 47: 1531-1534.

Waage et al., "Association between tumour necrosis factor in serum and fatal outcome in patients with meningococcal disease" (1987), Lancet 329(8529): 355-357.

Weilbach and Gold "Disease modifying treatments for multiple sclerosis" (1999), CNS Drugs 11(2): 133-157.

* cited by examiner

SOLUBLE TUMOR NECROSIS FACTOR RECEPTOR TREATMENT OF MEDICAL DISORDERS

This application is a divisional of U.S. application Ser. No. 10/853,479, filed May 25, 2004, now pending; which is a divisional of U.S. application Ser. No. 09/602,351, filed Jun. 23, 2000, now abandoned, which claims benefit of U.S. Provisional Application Nos. 60/164,676, filed Nov. 10, 1999, and 60/184,864, filed Feb. 25, 2000, and which is a continuation-in-part of U.S. application Ser. No. 09/373,828, filed Aug. 13, 1999, now abandoned, which claims the benefit of U.S. Provisional Application Nos. 60/130,074, filed Apr. 19, 1999, 60/134,320, filed May 14, 1999, 60/143,959, filed Jul. 15, 1999, and 60/148,234, filed Aug. 11, 1999; all of which are incorporated herein by reference in their entirety.

FIELD OF THE INVENTION

The invention pertains to methods for treating various medical disorders that are characterized by abnormal or excessive TNFα levels by administering a TNFα antagonist, preferably a soluble TNFα. The TNFα inhibitor may be administered in combination with other biologically active molecules.

BACKGROUND OF THE INVENTION

The pleiotropic cytokine tumor necrosis factor alpha (TNFα) is associated with inflammation and binds to cells through membrane receptor molecules, including two molecules having molecular weights of approximately 55 kDa and 75 kDa (p55 and p75). In addition to binding TNFα, the p55 and p75 TNF receptors mediate the binding to cells of homotrimers of TNFβ, which is another cytokine associated with inflammation and which shares structural similarities with TNFα (e.g., see Cosman, *Blood Cell Biochem* 7:51-77, 1996). TNFβ is also known as lymphotoxin-α (LTα).

It has been proposed that a systemic or localized excess of TNFα contributes to the progression of numerous medical disorders. For example, patients with chronic heart failure have elevated levels of serum TNFα, which have been shown to increase with disease progression (see, for example, Levine et al., *N Eng J Med* 323:236-241, 1990). A variety of other diseases are associated with elevated levels of TNFα (see, for example, Feldman et al., *Transplantation Proceedings* 30:4126-4127, 1998).

Psoriatic arthritis (PsA) is a chronic autoimmune condition that shares some features with both rheumatoid arthritis (RA) and the inflammatory skin disease psoriasis (for review, see Breathnach, In Klippel and Dieppe eds. *Rheumatology*, 2$^{nd}$ Ed., Mosby, 1998, 22.1-22.4). Psoriasis is characterized by epidermal keratinocyte hyperproliferation, accompanied by neutrophil and T cell infiltration, and is associated with elevated levels of inflammatory cytokines, including TNFα, IL-6 and TGFβ (see, for example, Bonifati et al., *Clin Exp Dermatol* 19:383-387, 1994). Psoriasis and PsA are different clinical entities, and are associated with somewhat different MHC haplotypes (Gladman, *Rheum Dis Clin NA*. 18:247-256, 1992; Breathnach, 1998). The overall prognosis for PsA is far worse than for ordinary psoriasis. Nonetheless, treatments used for the psoriatic lesions of PsA generally are similar to those used to treat psoriasis.

Psoriatic skin lesions are present in patients with PsA, although only a minority of psoriasis sufferers actually have PsA. Ordinary psoriasis occasionally is accompanied by joint pain, but does not involve the extreme pain and often deforming degeneration of joints and bone that occurs in PsA patients.

Treatments that sometimes are effective in treating ordinary psoriasis include topical medications (e.g., steroids, coal tar, anthralin, Dead Sea salts, various natural oils, vitamin D3 and its analogs, sunshine, topical retinoids), phototherapy (e.g., ultraviolet light, photochemotherapy (PUVA)), and internal medications (e.g., methotrexate, systemic steroids, oral retinoids, cyclosporine, or a rotating regimen of these three). In addition, it has been proposed that psoriasis could be treated with TNF-derived peptides, quinolinesulfonamides, pyrrolidinone derivatives, catechol diether compounds, isoxazoline compounds, matrix metalloproteinase inhibitors or mercapto alkyl peptidyl compounds, all of which inhibit either TNFα production or its release from cultured cells (see, for example, U.S. Pat. No. 5,691,382, U.S. Pat. No. 5,834,485, U.S. Pat. No. 5,420,154, U.S. Pat. No. 5,563,143, U.S. Pat. No. 5,869,511 and U.S. Pat. No. 5,872,146), as well as with various combination therapies involving TNFα antagonists (for example, see U.S. Pat. No. 5,888,511 or U.S. Pat. No. 5,958,413).

Conflicting results have been reported regarding the role of TNFα in psoriasis. Some investigators have proposed that overproduction of TNFα contributes to the pathology of psoriasis (e.g., Pigatto et al., *J. Invest Dermatol* 94:372-376, 1990; Sagawa et al., *Dermatol* 187:81-83, 1993; Ameglio et al., *Dermatol* 189:359-363, 1994). One group reported some improvement after treatment with pentoxifylline, a drug that can inhibit the release of TNFα, but which exerts many of its physiological effects by inhibiting cyclic AMP phosphodiesterase (Omulecki et al., *J Am Acad Dermatol* 34:714-715, 1996; Centola et al., *J Androl* 16:136-142, 1995; Elferinck et al., *Biochem Pharmacol* 54:475-480, 1997). However, other reports have cast doubt on the hypothesis that overproduction of TNFα exacerbates psoriasis. For example, some investigators have reported that treatment with TNFα itself actually can mitigate psoriasis (see, e.g., Takematsu et al., *Br J Dermatol* 124:209-210, 1991; Creaven et al., *J Am Acad Dermatol* 24:735-737, 1991).

In addition to psoriatic lesions, PsA is characterized by distal interphalangeal joint (DIP) involvement, enthesopathy, nail lesions, spondylitis and dactylitis. The histopathogenesis of PsA and the more well-studied rheumatoid arthritis share certain features. In both RA and in active PsA, patients exhibit increased levels of HLA-DR[+] T cells and MHC class II antigens in their synovial membranes and synovial fluid, as well as increased expression of the cytokine TNFα. In addition, both diseases are associated with prominent synovial vascular changes.

The discovery of rheumatoid factor in the serum of RA patients provided an important tool for differentiating PsA from RA, but the realization that RA and PsA are distinct diseases was based primarily on their many clinical differences (e.g., Helliwell and Wright, In Klippel and Dieppe eds. *Rheumatology*, 2$^{nd}$ Ed., Mosby, 1998, 21.1-21.8). Studies have shown that levels of TNFα, Il-1β, Il-8 as well as TNFα receptors in synovial fluids were higher in PsA patients than in osteoarthritis patients, though they were lower than in RA patients (Partsch et al., *J Rheumatol* 24:518-523, 1997; Partsch et al., *J Rheumatol* 25:105-110, 1998; Partsch et al., *Ann Rheum Dis* 57:691-693, 1998). PsA is distinguished from RA also by radiographic appearance, a notably higher degree of synovial membrane vascularity as well as differences in the levels of various cytokines in the synovial fluids (Ritchlin et al., *J Rheumatol* 25:1544-52, 1998; Veale et al., *Arth Rheum* 36:893-900, 1993). Veale et al. noted differences in synovial membrane adhesion molecules and numbers of macrophages when they compared RA and PsA patients, as well as observing a minimal degree of hyperplasia and hypertrophy of synoviocytes in PsA as compared with RA patients. Because of such differences, coupled with the association of PsA but not RA with class I MHC antigens, Ritchlin et al. have suggested that PsA must be triggered by different mechanisms than those underlying RA. Veale et al. suggested for similar reasons that different cytokines were likely to be interacting in the synovium of PsA and RA patients.

Most of the drugs used for treating the arthritic aspects of PsA are similar to those used in RA (Salvarini et al., *Curr Opin Rheumatol* 10:229-305, 1998), for example the nonsteroidal antiinflammatories (NSAIDs), which may be used alone or in combination with the disease-modifying antirheumatic drugs, or "DMARDs." However, one group found that long-term administration of the DMARD methotrexate failed to slow the progression of joint damage in PsA patients (Abu-Shakra et al., *J Rheumatol* 22:241-45, 1995), and another group reported very little improvement in PsA patients who had received methotrexate (Willkens et al., *Arthr Rheum* 27:376-381, 1984). Similarly, Clegg et al. found only a slight improvement over placebo in PsA patients treated with sulfasalazine, another drug classified as a DMARD (Clegg et al., *Arthritis Rheum* 39: 2013-20, 1996). Some studies have indicated that the immunosuppressor cyclosporine is effective in treating PsA (reviewed in Salvarini et al., 1998), though this drug has severe side effects. In addition, others have proposed that PsA could be treated with truncated TNFα receptors or with a combination of methotrexate and antibodies against TNFα (WO 98/01555; WO 98/0537).

A recent meta-analysis of a number of PsA treatment studies concluded that PsA and RA differed not only in their response to treatment with specific drugs, but in the relative magnitudes of improvement in the placebo arms of the studies (Jones et al., *Br J Rheumatol* 36:95-99, 1997). As an example, PsA patients responded better to gold salt therapy than did RA patients, though the gold did not affect the psoriatic skin lesions (Dorwart et al., *Arthritis Rheum* 21:515-513, 1978).

It has been suggested that the suppression of TNFα might be beneficial in patients suffering from various disorders characterized by abnormal or excessive TNFα expression. However, although progress has been made in devising effective treatment for such diseases, improved medicaments and methods of treatment are needed.

SUMMARY OF THE INVENTION

Provided herein are methods for treating a number of medical disorders characterized by abnormal TNFα expression by repeatedly administering an antagonist of TNFα, such as a soluble TNFα receptor, for a period of time sufficient to induce a sustained improvement in the patient's condition.

DETAILED DESCRIPTION OF THE INVENTION

This invention provides compounds, compositions and methods for treating a mammalian patient, including a human patient, who is suffering from a medical disorder that is characterized by abnormal or elevated expression of TNFα. For purposes of this disclosure, the terms "illness," "disease," "medical condition," "abnormal condition" and the like are used interchangeably with the term "medical disorder."

The subject methods involve administering to the patient a soluble TNFα antagonist that is capable of reducing the effective amount of endogenous biologically active TNFα, such as by reducing the amount of TNFα produced, or by preventing the binding of TNFα to its cell surface receptor (TNFR). Antagonists capable of inhibiting this binding include receptor-binding peptide fragments of TNFα, antibodies directed against TNFα, and recombinant proteins comprising all or portions of receptors for TNFα or modified variants thereof, including genetically-modified muteins, multimeric forms and sustained-release formulations. Other compounds suitable for treating the diseases described herein include thalidomide and pentoxifylline.

Preferred embodiments of the invention utilize soluble TNFRs as the TNFα antagonist. Soluble forms of TNFRs may include monomers, fusion proteins (also called "chimeric proteins"), dimers, trimers or higher order multimers. In certain embodiments of the invention, the soluble TNFR derivative is one that mimics the 75 kDa TNFR or the 55 kDa TNFR and that binds to TNFα in the patient's body. The soluble TNFR mimics of the present invention may be derived from TNFRs p55 or p75 or fragments thereof. TNFRs other than p55 and p75 also are useful for deriving soluble compounds for treating the various medical disorders described herein, such for example the TNFR described in WO 99/04001. Soluble TNFR molecules used to construct TNFR mimics include, for example, analogs or fragments of native TNFRs having at least 20 amino acids, that lack the transmembrane region of the native TNFR, and that are capable of binding TNFα. Antagonists derived from TNFRs compete for TNFα with the receptors on the cell surface, thus inhibiting TNFα from binding to cells, thereby preventing it from manifesting its biological activities. Binding of soluble TNFRs to TNFα or LTα can be assayed using ELISA or any other convenient assay. This invention provides for the use of soluble TNFα receptors in the manufacture of medicaments for the treatment of numerous diseases.

The soluble TNFR polypeptides or fragments of the invention may be fused with a second polypeptide to form a chimeric protein. The second polypeptide may promote the spontaneous formation by the chimeric protein of a dimer, trimer or higher order muimer that is capable of binding a TNFα and/or LTα molecule and preventing it from binding to cell-bound receptors. Chimeric proteins used as antagonists include, for example, molecules derived from an antibody molecule and a TNFR. Such molecules are referred to herein as TNFR-Ig fusion proteins. A preferred TNFR-Ig fusion protein suitable for treating diseases in humans and other mammals is recombinant TNFR:Fc, a term which as used herein refers to "etanercept," which is a dimer of two molecules of the extracellular portion of the p75 TNFα receptor, each molecule consisting of a 235 amino acid TNFR-derived polypeptide that is fused to a 232 amino acid Fc portion of human IgG$_1$. Etanercept is currently sold by Immunex Corporation under the trade name ENBREL.® Because the p75 receptor protein that it incorporates binds not only to TNFα, but also to the inflammatory cytokine LTα, etanercept can act as a competitive inhibitor not only of TNFα, but also of LTα. This is in contrast to antibodies directed against TNFα, which cannot inhibit LTα. Also encompassed by the invention are treatments using a compound that comprises the extracellular portion of the 55 kDa TNFR fused to the Fc portion of IgG, as well as compositions and combinations containing such a molecule. Encompassed also are therapeutic methods involving the administration of TNFR-Ig proteins derived the extracellular regions of TNFα receptor molecules other than the p55 and p75 TNFRs, such as for example the TNFR described in WO 99/04001.

In one preferred embodiment of the invention, sustained-release forms of soluble TNFRs are used, including sustained-release forms of TNFR:Fc. Sustained-release forms suitable for use in the disclosed methods include, but are not limited to, TNFRs that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant. In addition, the soluble TNFR may be conjugated with polyethylene glycol (pegylated) to prolong its serum half-life or to enhance protein delivery.

In accord with this invention, medical disorders characterized by abnormal or excess expression of TNFα are administered a therapeutically effective amount of a TNFα inhibitor. The TNFα inhibitor may be a TNFα-binding soluble TNFα receptor, preferably TNFR:Fc. As used herein, the phrase "administering a therapeutically effective amount" of a therapeutic agent means that the patient is treated with the agent in an amount and for a time sufficient to induce a sustained improvement in at least one indicator that reflects the severity of the disorder. An improvement is considered "sustained" if the patient exhibits the improvement on at least two occasions separated by one or more weeks. The degree of improvement is determined based on signs or symptoms, and determinations may also employ questionnaires that are administered to the patient, such as quality-of-life questionnaires.

Various indicators that reflect the extent of the patient's illness may be assessed for determining whether the amount and time of the treatment is sufficient. The baseline value for the chosen indicator or indicators is established by examination of the patient prior to administration of the first dose of the etanercept or other TNFα inhibitor. Preferably, the baseline examination is done within about 60 days of administering the first dose. If the TNFα antagonist is being administered to treat acute symptoms, such as for example to treat a traumatic knee injury, the first dose is administered as soon as practically possible after the injury has occurred.

Improvement is induced by administering TNFR:Fc or other TNFα antagonist until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Any efficacious route of administration may be used to therapeutically administer TNFR:Fc or other TNFα antagonists. If injected, TNFR:Fc can be administered, for example, via intra-articular, intravenous, intramuscular, intralesional, intraperitoneal or subcutaneous routes by bolus injection or by continuous infusion. Other suitable means of administration include sustained release from implants, aerosol inhalation, eyedrops, oral preparations, including pills, syrups, lozenges or chewing gum, and topical preparations such as lotions, gels, sprays, ointments or other suitable techniques. Alternatively, proteinaceous TNFα inhibitors, such as a soluble TNFR, may be administered by implanting cultured cells that express the protein, for example, by implanting cells that express TNFR:Fc. In one embodiment, the patient's own cells are induced to produce TNFR:Fc by transfection in vivo or ex vivo with a DNA that encodes TNFR:Fc. This DNA can be introduced into the patient's cells, for example, by injecting naked DNA or liposome-encapsulated DNA that encodes TNFR:Fc, or by other means of transfection. When TNFR:Fc is administered in combination with one or more other biologically active compounds, these may be administered by the same or by different routes, and may be administered simultaneously, separately or sequentially.

TNFR:Fc or other soluble TNFRs preferably are administered in the form of a physiologically acceptable composition comprising purified recombinant protein in conjunction with physiologically acceptable carriers, excipients or diluents. Such carriers are nontoxic to recipients at the dosages and concentrations employed. Ordinarily, the preparation of such compositions entails combining the TNFα antagonist with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. Neutral buffered saline or saline mixed with conspecific serum albumin are exemplary appropriate diluents. In accordance with appropriate industry standards, preservatives may also be added, such as benzyl alcohol. TNFR:Fc preferably is formulated as a lyophilizate using appropriate excipient solutions (e.g., sucrose) as diluents. Appropriate dosages can be determined in standard dosing trials, and may vary according to the chosen route of administration. The amount and frequency of administration will depend, of course, on such factors as the nature and severity of the indication being treated, the desired response, the age and condition of the patient, and so forth.

In one embodiment of the invention, TNFR:Fc is administered one time per week to treat the various medical disorders disclosed herein, in another embodiment is administered at least two times per week, and in another embodiment is administered at least three times per week. An adult patient is a person who is 18 years of age or older. If injected, the effective amount of TNFR:Fc per adult dose ranges from 1-20 mg/m$^2$, and preferably is about 5-12 mg/m$^2$. Alternatively, a flat dose may be administered, whose amount may range from 5-100 mg/dose. Exemplary dose ranges for a flat dose to be administered by subcutaneous injection are 5-25 mg/dose, 25-50 mg/dose and 50-100 mg/dose. In one embodiment of the invention, the various indications described below are treated by administering a preparation acceptable for injection containing TNFR:Fc at 25 mg/dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of TNFR:Fc one to three times per week over a period of at least three weeks, or a dose of 50 mg of TNFR:Fc one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the patient's physician.

For pediatric patients (age 4-17), a suitable regimen involves the subcutaneous injection of 0.4 mg/kg, up to a maximum dose of 25 mg of TNFR:Fc, administered by subcutaneous injection one or more times per week.

The invention further includes the administration of TNFR:Fc concurrently with one or more other drugs that are administered to the same patient in combination with the TNFR:Fc, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. Examples of drugs to be administered concurrently include but are not limited to antivirals, antibiotics, analgesics, corticosteroids, antagonists of inflammatory cytokines, DMARDs and non-steroidal anti-inflammatories. DMARDs that can be administered in combination with the subject TNFα inhibitors such as TNFR:Fc include azathioprine, cyclophosphamide, cyclosporine, hydroxychloroquine sulfate, methotrexate, leflunomide, minocycline, penicillamine, sulfasalazine and gold compounds such as oral gold, gold sodium thiomalate and aurothioglucose. Additionally, TNFR:Fc may be combined with a second TNFα antagonist, including an antibody against TNFα or TNFR, a TNFα-derived peptide that acts as a competitive inhibitor of TNFα (such as those described in U.S. Pat. No. 5,795,859), a TNFR-IgG fusion protein other than etanercept, such as one containing the extracellular portion of the p55 TNFα receptor, a soluble TNFR other than an IgG fusion protein, or other molecules that reduce endogenous TNFα levels, such as inhibitors of the TNFα converting enzyme (see e.g., U.S. Pat. No. 5,594,106). In further embodiments of this invention, TNFR:Fc is administered in combination with pentoxifylline or thalidomide.

If an antibody against TNFα is used as the TNFα inhibitor, a preferred dose range is 0.1 to 20 mg/kg, and more preferably is 1-10 mg/kg. Another preferred dose range for anti-TNFα antibody is 0.75 to 7.5 mg/kg of body weight. Humanized antibodies are preferred, that is, antibodies in which only the antigen-binding portion of the antibody molecule is derived from a non-human source. such antibodies may be injected or administered intravenously.

In one preferred embodiment of the invention, the various medical disorders disclosed herein as being treatable with inhibitors such as TNFR:Fc are treated in combination with another cytokine or cytokine inhibitor. For example, TNFR:Fc may be administered in a composition that also contains a compound that inhibits the interaction of other inflammatory cytokines with their receptors. Examples of cytokine inhibitors used in combination with TNFR:Fc include, for example, antagonists of TGFβ, Il-6 or Il-8. TNFα inhibitors such as TNFR:Fc also may be administered in combination with the cytokines GM-CSF, IL-2 and inhibitors of protein kinase A type 1 to enhance T cell proliferation in HIV-infected patients who are receiving anti-retroviral therapy. Other combinations for treating the herein described diseases include TNFR:Fc administered concurrently with compounds that block the binding of RANK and RANK-ligand, such as antagonistic antibodies against RANK or RANK-ligand, soluble forms of RANK-ligand that do not trigger RANK, osteoprotegerin or soluble forms of RANK, including RANK:Fc. Soluble forms of RANK suitable for these combinations are described, for example, in U.S. Pat. No. 6,017,729. The concurrent administration of TNFR:Fc and RANK:Fc or TNFR:Fc and osteoprotegerin is useful for preventing bone destruction in various settings including but not limited to various rheumatic disorders, osteoporosis, multiple myeloma or other malignancies that cause bone degeneration, or anti-tumor therapy aimed at preventing metastasis to bone, or bone destruction associated with prosthesis wear debris or with periodontitis.

The present invention also relates to the use of the disclosed TNFα inhibitors, such as TNFR:Fc, in the manufacture of a medicament for the prevention or therapeutic treatment of each medical disorder disclosed herein.

The disclosed TNFα inhibitors, compositions and combination therapies described herein are useful in medicines for treating bacterial, viral or protozoal infections, and complications resulting therefrom. One such disease is *Mycoplasma pneumonia*. In addition, provided herein is the use of TNFR:Fc to treat AIDS and related conditions, such as AIDS dementia complex, AIDS associated wasting, lipidistrophy due to antiretroviral therapy; and Kaposi's sarcoma. Provided herein is the use of TNFR:Fc for treating protozoal diseases, including malaria and schistosomiasis. Additionally provided is the use of TNFR:Fc to treat erythema nodosum leprosum; bacterial or viral meningitis; tuberculosis, including pulmonary tuberculosis; and pneumonitis secondary to a bacterial or viral infection. Provided also herein is the use of TNFR:Fc to prepare medicaments for treating louse-borne relapsing fevers, such as that caused by *Borrelia recurrentis*. TNFR:Fc can also be used to prepare a medicament for treating conditions caused by Herpes viruses, such as herpetic stromal keratitis, corneal lesions, and virus-induced corneal disorders. In addition, TNFR:Fc can be used in treating human papillomavirus infections. TNFR:Fc is used also to prepare medicaments to treat influenza.

Cardiovascular disorders are treatable with the disclosed TNFα inhibitors, pharmaceutical compositions or combination therapies, including aortic aneurisms; arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure (CHF), cachexia of heart failure; myocardial infarction; restenosis after heart surgery; silent myocardial ischemia; post-implantation complications of left ventricular assist devices; Raynaud's phenomena; thrombophlebitis; vasculitis, including Kawasaki's vasculitis; giant cell arteritis, Wegener's granulomatosis; and Schoenlein-Henoch purpura.

TNFα and IL-8 have been implicated as chemotactic factors in athersclerotic abdominal aortic aneurism (Szekanecz et al., *Pathobiol* 62:134-139 (1994)). Abdominal aortic aneurism may be treated in human patients by administering a soluble TNFR, such as TNFR:Fc, which may be administered in combination with an inhibitor of IL-8, such treatment having the effect of reducing the pathological neovascularization associated with this condition.

A combination of a TNFα inhibitor and one or more other anti-angiogenesis factors may be used to treat solid tumors, thereby reducing the vascularization that nourishes the tumor tissue. Suitable anti-angiogenic factors for such combination therapies include IL-8 inhibitors, angiostatin, endostatin, kringle 5, inhibitors of vascular endothelial growth factor (such as antibodies against vascular endothelial growth factor), angiopoietin-2 or other antagonists of angiopoietin-1, antagonists of platelet-activating factor and antagonists of basic fibroblast growth factor In addition, the subject TNFα inhibitors, compositions and combination therapies are used to treat chronic pain conditions, such as chronic pelvic pain, including chronic prostatitis/pelvic pain syndrome. As a further example, TNFR:Fc and the compositions and combination therapies of the invention are used to treat post-herpetic pain.

Provided also are methods for using TNFα inhibitors, compositions or combination therapies to treat various disorders of the endocrine system. For example, the TNFα inhibitors are used to treat juvenile onset diabetes (includes autoimmune and insulin-dependent types of diabetes) and also to treat maturity onset diabetes (includes non-insulin dependent and obesity-mediated diabetes). In addition, the subject compounds, compositions and combination therapies are used to treat secondary conditions associated with diabetes, such as diabetic retinopathy, kidney transplant rejection in diabetic patients, obesity-mediated insulin resistance, and renal failure, which itself may be associated with proteinurea and hypertension. Other endocrine disorders also are treatable with these compounds, compositions or combination therapies, including polycystic ovarian disease, X-linked adrenoleukodystrophy, hypothyroidism and thyroiditis, including Hashimoto's thyroiditis (i.e., autoimmune thyroiditis).

Conditions of the gastrointestinal system also are treatable with TNFα inhibitors, compositions or combination therapies, including coeliac disease. In addition, the compounds, compositions and combination therapies of the invention are used to treat Crohn's disease; ulcerative colitis; idiopathic gastroparesis; pancreatitis, including chronic pancreatitis and lung injury associated with acute pancreatitis; and ulcers, including gastric and duodenal ulcers.

Included also are methods for using the subject TNFα inhibitors, compositions or combination therapies for treating disorders of the genitourinary system, such as glomerulonephritis, including autoimmune glomerulonephritis, glomerulonephritis due to exposure to toxins or glomerulonephritis secondary to infections with haemolytic streptococci or other infectious agents. Also treatable with the compounds, compositions and combination therapies of the invention are uremic syndrome and its clinical complications (for example, renal failure, anemia, and hypertrophic cardiomyopathy), including uremic syndrome associated with exposure to environmental toxins, drugs or other causes. Further conditions treatable with the compounds, compositions and combination therapies of the invention are complications of hemodialysis; prostate conditions, including benign prostatic hypertrophy, nonbacterial prostatitis and chronic prostatitis; and complications of hemodialysis.

Also provided herein are methods for using TNFα inhibitors, compositions or combination therapies to treat various hematologic and oncologic disorders. For example, TNFR:Fc is used to treat various forms of cancer, including acute myelogenous leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. Additional diseases treatable with the subject TNFα inhibitors, compositions or combination therapies are solid tumors, including sarcoma, osteosarcoma, and carcinoma, such as adenocarcinoma (for example, breast cancer) and squamous cell carcinoma. In addition, the subject compounds, compositions or combination therapies are useful for treating leukemia, including acute myelogenous leukemia, chronic or acute lymphoblastic leukemia and hairy cell leukemia. Other malignancies with invasive metastatic potential can be treated with the subject compounds, compositions and combination therapies, including multiple myeloma. In addition, the disclosed TNFα inhibitors, compositions and combination therapies can be used to treat anemias and hematologic disorders, including anemia of chronic disease, aplastic anemia, including Fanconi's aplastic anemia; idiopathic thrombocytopenic purpura (ITP); myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis.

Various lymphoproliferative disorders also are treatable with the disclosed TNFα inhibitors, compositions or combination therapies. These include, but are not limited to autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sézary syndrome.

In addition, the subject TNFα inhibitors, compositions and combination therapies are used to treat hereditary conditions such as Gaucher's disease, Huntington's disease, linear IgA disease, and muscular dystrophy.

Other conditions treatable by the disclosed TNFα inhibitors, compositions and combination therapies include those resulting from injuries to the head or spinal cord, and including subdural hematoma due to trauma to the head.

The disclosed TNFα inhibitors, compositions and combination therapies are further used to treat conditions of the liver such as hepatitis, including acute alcoholic hepatitis, acute drug-induced or viral hepatitis, hepatitis A, B and C, sclerosing cholangitis and inflammation of the liver due to unknown causes.

In addition, the disclosed TNFα inhibitors, compositions and combination therapies are used to treat various disorders that involve hearing loss and that are associated with abnormal TNFα expression. One of these is inner ear or cochlear nerve-associated hearing loss that is thought to result from an autoimmune process, i.e., autoimmune hearing loss. This condition currently is treated with steroids, methotrexate and/or cyclophosphamide, which may be administered concurrently with the TNFR:Fc or other TNFα inhibitor. Also treatable with the disclosed TNFα inhibitors, compositions and combination therapies is cholesteatoma, a middle ear disorder often associated with hearing loss.

In addition, the subject invention provides TNFα inhibitors, compositions and combination therapies for the treatment of non-arthritic medical conditions of the bones and joints. This encompasses osteoclast disorders that lead to bone loss, such as but not limited to osteoporosis, including post-menopausal osteoporosis, periodontitis resulting in tooth loosening or loss, and prosthesis loosening after joint replacement (generally associated with an inflammatory response to wear debris). This latter condition also is called "orthopedic implant osteolysis." Another condition treatable by administering TNFRα inhibitors, such as TNFR:Fc, is temporal mandibular joint dysfunction (TMJ).

A number of pulmonary disorders also can be treated with the disclosed TNFα inhibitors, compositions and combination therapies. One such condition is adult respiratory distress syndrome (ARDS), which is associated with elevated TNFα, and may be triggered by a variety of causes, including exposure to toxic chemicals, pancreatitis, trauma or other causes. The disclosed compounds, compositions and combination therapies of the invention also are useful for treating bronchopulmonary dysplasia (BPD); lymphangioleiomyomatosis; and chronic fibrotic lung disease of preterm infants. In addition, the compounds, compositions and combination therapies of the invention are used to treat occupational lung diseases, including asbestosis, coal worker's pneumoconiosis, silicosis or similar conditions associated with long-term exposure to fine particles. In other aspects of the invention, the disclosed compounds, compositions and combination therapies are used to treat pulmonary disorders, including chronic obstructive pulmonary disease (COPD) associated with chronic bronchitis or emphysema; fibrotic lung diseases, such as cystic fibrosis, idiopathic pulmonary fibrosis and radiation-induced pulmonary fibrosis; pulmonary sarcoidosis; and allergies, including allergic rhinitis, contact dermatitis, atopic dermatitis and asthma.

Cystic fibrosis is an inherited condition characterized primarily by the accumulation of thick mucus, predisposing the patient to chronic lung infections and obstruction of the pancreas, which results in malabsorption of nutrients and malnutrition. TNFR:Fc may be administered to treat cystic fibrosis. If desired, treatment with TNFR:Fc may be administered concurrently with corticosteroids, mucus-thinning agents such as inhaled recombinant deoxyribonuclease I (such as PULMOZYME®; Genentech, Inc.) or inhaled tobramycin (TOBI®; Pathogenesis, Inc.). TNFR:Fc also may be administered concurrently with corrective gene therapy, drugs that stimulate cystic fibrosis cells to secrete chloride or other yet-to-be-discovered treatments. Sufficiency of treatment may be assessed, for example, by observing a decrease in the number of pathogenic organisms in sputum or lung lavage (such as *Haemophilus influenzae, Stapholococcus aureus*, and *Pseudomonas aeruginosa*), by monitoring the patient for weight gain, by detecting an increase in lung capacity or by any other convenient means.

TNFR:Fc or TNFR:Fc combined with the cytokine IFNγ-1b (such as ACTIMMUNE®; InterMune Pharmaceuticals) may be used for treating cystic fibrosis or fibrotic lung diseases, such as idiopathic pulmonary fibrosis, radiation-induced pulmonary fibrosis and bleomycin-induced pulmonary fibrosis. In addition, this combination is useful for treating other diseases characterized by organ fibrosis, including systemic sclerosis (also called "scleroderma"), which often involves fibrosis of the liver. For treating cystic fibrosis, TNFR:Fc and IFNγ-1b may be combined with PULMOZYMEL® or TOBI® or other treatments for cystic fibrosis.

TNFR:Fc alone or in combination with IFNγ-1b may be administered together with other treatments presently used for treating fibrotic lung disease. Such additional treatments include glucocorticoids, azathioprine, cyclophosphamide, penicillamine, colchisicine, supplemental oxygen and so forth. Patients with fibrotic lung disease, such as IPF, often present with nonproductive cough, progressive dyspnea, and show a restrictive ventilatory pattern in pulmonary function tests. Chest radiographs reveal fibrotic accumulations in the patient's lungs. When treating fibrotic lung disease in accord with the disclosed methods, sufficiency of treatment may be detected by observing a decrease in the patient's coughing (when cough is present), or by using standard lung function tests to detect improvements in total lung capacity, vital capacity, residual lung volume or by administering a arterial blood gas determination measuring desaturation under exercising conditions, and showing that the patient's lung function has improved according to one or more of these measures. In addition, patient improvement may be determined through chest radiography results showing that the progression of fibrosis in the patient's lungs has become arrested or reduced.

In addition, TNF inhibitors (including soluble TNFRs or antibodies against TNFα or TNFR) are useful for treating organ fibrosis when administered in combination with relaxin, a hormone that down-regulates collagen production thus inhibiting fibrosis, or when given in combination with agents that block the fibrogenic activity of TGF-β. Combination therapies using TNFR:Fc and recombinant human relaxin are useful, for example, for treating systemic sclerosis or fibrotic lung diseases, including cystic fibrosis, idiopathic pulmonary fibrosis, radiation-induced pulmonary fibrosis and bleomycin-induced pulmonary fibrosis.

Other embodiments provide methods for using the disclosed TNFα inhibitors, compositions or combination therapies to treat a variety of rheumatic disorders. These include: adult and juvenile rheumatoid arthritis; systemic lupus erythematosus; gout; osteoarthritis; polymyalgia rheumatica; seronegative spondylarthropathies, including ankylosing spondylitis; and Reiter's disease. The subject TNFα inhibitors, compositions and combination therapies are used also to treat psoriatic arthritis and chronic Lyme arthritis. Also treatable with these compounds, compositions and combination therapies are Still's disease and uveitis associated with rheumatoid arthritis. In addition, the compounds, compositions and combination therapies of the invention are used in treating disorders resulting in inflammation of the voluntary muscle, including dermatomyositis and polymyositis. Moreover, the compounds, compositions ant combinations disclosed herein are useful for treating sporadic inclusion body myositis, as TNFα may play a significant role in the progression of this muscle disease. In addition, the compounds, compositions and combinations disclosed herein are used to treat multicentric reticulohistiocytosis, a disease in which joint destruction and papular nodules of the face and hands are associated with excess production of proinflammatory cytokines by multinucleated giant cells.

For purposes of this invention, patients are defined as having psoriatic arthrisis (PsA) if they have one or more swollen joints or one or more painful or tender joints, and also manifest at least one psoriatic lesion of the skin or nails. The psoriatic lesions may appear before or after the onset of swollen or tender joints. It is understood that prior to treatment, manifestations of PsA may have persisted over time, e.g., for several months or years, and may involve several joints. According to one classification system (reviewed in Alonso et al., 1991), PsA patients can be categorized based on their arthritic symptoms into five clinical subgroups: 1) DIP; 2) mutilans arthritis; 3) symmetrical polyarthritis; 4) oligoarticular arthritis; and 5) ankylosing spondylitis-like. The disclosed therapies, compounds and compositions are suitable for treating all five forms of PsA.

The TNFα inhibitors, compositions and combination therapies of the invention may be used to inhibit hypertrophic scarring, a phenomenon believed to result in part from excessive TNFα secretion. TNF inhibitors may be administered alone or concurrently with other agents that inhibit hypertrophic scarring, such as inhibitors of TGF-α.

Cervicogenic headache is a common form of headache arising from dysfunction in the neck area, and which is associated with elevated levels of TNFα, which are believed to mediate an inflammatory condition that contributes to the patient's discomfort (Martelletti, *Clin Exp Rheumatol* 18(2 Suppl 19):S33-8 (March-April, 2000)). Cervicogenic headache may be treated by administering an inhibitor of TNFα as disclosed herein, thereby reducing the inflammatory response and associated headache pain.

The TNFα inhibitors, compositions and combination therapies of the invention are useful for treating primary amyloidosis. In addition, the secondary amyloidosis that is characteristic of various conditions also are treatable with TNFα inhibitors such as TNFR:Fc, and the compositions and combination therapies described herein. Such conditions include: Alzheimer's disease, secondary reactive amyloidosis; Down's syndrome; and dialysis-associated amyloidosis. Also treatable with the compounds, compositions and combination therapies of the invention are inherited periodic fever syndromes, including familial Mediterranean fever, hyperimmunoglobulin D and periodic fever syndrome and TNF-receptor associated periodic syndromes (TRAPS).

Disorders associated with transplantation also are treatable with the disclosed TNFα inhibitors, compositions or combination therapies, such as graft-versus-host disease, and complications resulting from solid organ transplantation, including transplantion of heart, liver, lung, skin, kidney or other organs. TNFR:Fc may be administered, for example, to prevent or inhibit the development of bronchiolitis obliterans after lung transplantation. Patients undergoing autologous hematopoietic stem cell transplantation in the form of peripheral blood stem cell transplantation may develop "engraftment syndrome," or "ES," which is an adverse and generally self-limited response that occurs about the time of hematopoietic engraftment and which can result in pulmonary deterioration. ES may be treated with inhibitors of either IL-8 or TNFα (such as TNFR:Fc), or with a combination of inhibitors against both of these cytokines.

Ocular disorders also are treatable with the disclosed TNFα inhibitors, compositions or combination therapies, including rhegmatogenous retinal detachment, and inflammatory eye disease, and inflammatory eye disease associated with smoking and macular degeneration.

TNFα inhibitors such as TNFR:Fc and the disclosed compositions and combination therapies also are useful for treating disorders that affect the female reproductive system. Examples include, but are not limited to, multiple implant failure/infertility; fetal loss syndrome or IV embryo loss (spontaneous abortion); preeclamptic pregnancies or eclampsia; and endometriosis.

In addition, the disclosed TNFα inhibitors, compositions and combination therapies are useful for treating obesity, including treatment to bring about a decrease in leptin formation. Also, the compounds, compositions and combination therapies of the invention are used to treat sciatica, symptoms of aging, severe drug reactions (for example, Il-2 toxicity or bleomycin-induced pneumopathy and fibrosis), or to suppress the inflammatory response prior, during or after the transfusion of allogeneic red blood cells in cardiac or other surgery, or in treating a traumatic injury to a limb or joint, such as traumatic knee injury. Various other medical disorders treatable with the disclosed TNFα inhibitors, compositions and combination therapies include; multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies.

The disclosed TNFα inhibitors, compositions and combination therapies furthermore are useful for treating acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; myasthenia gravis; silent cerebral ischemia; sleep disorders, including narcolepsy and sleep apnea; chronic neuronal degeneration; and stroke, including cerebral ischemic diseases.

Disorders involving the skin or mucous membranes also are treatable using the disclosed TNFα inhibitors, compositions or combination therapies. Such disorders include acantholytic diseases, including Darier's disease, keratosis follicularis and pemphigus vulgaris. Also treatable with the subject TNFα inhibitors, compositions and combination therapies are acne; acne rosacea; alopecia areata; aphthous stomatitis; bullous pemphigoid; burns; eczema; erythema, including erythema multiforme and erythema multiforme bullosum (Stevens-Johnson syndrome); inflammatory skin disease; lichen planus; linear IgA bullous disease (chronic bullous dermatosis of childhood); loss of skin elasticity; mucosal surface ulcers; neutrophilic dermatitis (Sweet's syndrome); pityriasis rubra pilaris; psoriasis; pyoderma gangrenosum; and toxic epidermal necrolysis.

Patients are defined as having ordinary psoriasis if they lack the more serious symptoms of PsA (e.g., distal interphalangeal joint DIP involvement, enthesopathy, spondylitis and dactylitis) but have one of the following: 1) inflamed swollen skin lesions covered with silvery white scale (plaque psoriasis or psoriasis vulgaris); 2) small red dots appearing on the trunk, arms or legs (guttate psoriasis); 3) smooth inflamed lesions without scaling in the flexural surfaces of the skin (inverse psoriasis); 4) widespread reddening and exfoliation of fine scales, with or without itching and swelling (erythrodermic psoriasis); 5) blister-like lesions (pustular psoriasis); 6) elevated inflamed scalp lesions covered by silvery white scales (scalp psoriasis); 7) pitted fingernails, with or without yellowish discoloration, crumbling nails, or inflammation and detachment of the nail from the nail bed (nail psoriasis).

Ordinary psoriasis may be treated by administering to a human patient compositions containing a therapeutically effective amount of a TNFα inhibitor such as a soluble TNF receptor or an antibody against TNFα.

In one preferred embodiment, the therapeutic agent is a soluble TNF receptor, and preferably is a TNFR-Ig. In a preferred embodiment, the TNFR-Ig is TNFR:Fc, which may be administered in the form of a pharmaceutically acceptable composition as described herein. Psoriasis may be treated by administering TNFR:Fc one or more times per week by subcutaneous injection, although other routes of administration may be used if desired. In one exemplary regimen for treating adult human patients, 25 mg of TNFR:Fc is administered by subcutaneous injection two times per week or three times per week for one or more weeks, and preferably for four or more weeks. Alternatively, a dose of 5-12 mg/m$^2$ or a flat dose of 50 mg is injected subcutaneously one time or two times per week for one or more weeks. In other embodiments, psoriasis is treated with TNFR:Fc in a sustained-release form, such as TNFR:Fc that is encapsulated in a biocompatible polymer, TNFR:Fc that is admixed with a biocompatible polymer (such as topically applied hydrogels), and TNFR:Fc that is encased in a semi-permeable implant.

Various other medicaments used to treat ordinary psoriasis may also be administered concurrently with compositions comprising TNFα inhibitors, such as TNFR:Fc. Such medicaments include: NSAIDs; DMARDs; analgesics; topical steroids; systemic steroids (e.g., prednisone); cytokines; antagonists of inflammatory cytokines; antibodies against T cell surface proteins; anthralin; coal tar; vitamin D3 and its analogs; topical retinoids; oral retinoids; salicylic acid; and hydroxyurea. Suitable analgesics for such combinations include: acetaminophen, codeine, propoxyphene napsylate, oxycodone hydrochloride, hydrocodone bitartrate and tramadol. DMARDs suitable for such combinations include: azathioprine, cyclophosphamide, cyclosporine, hydroxychloroquine sulfate, methotrexate, leflunomide, minocycline, penicillamine, sulfasalazine, oral gold, gold sodium thiomalate and aurothioglucose. In addition, the TNFR:Fc or other TNFR mimic may be administered in combination with antimalarials or colchicine. NSAIDs suitable for the subject combination treatments of psoriasis include: salicylic acid (aspirin) and salicylate derivatives; ibuprofen; indomethacin; celecoxib; rofecoxib; ketorolac; nambumetone; piroxicam; naproxen; oxaprozin; sulindac; ketoprofen; diclofenac; and other COX-1 and COX-2 inhibitors, propionic acid derivatives, acetic acid derivatives, fumaric acid derivatives, carboxylic acid derivatives, butyric acid derivatives, oxicams, pyrazoles and pyrazolones, including newly developed anti-inflammatories.

If an antagonist against an inflammatory cytokine is administered concurrently with TNFR:Fc to treat psoriasis, suitable targets for such antagonists include TGFβ, Il-6 and Il-8.

In addition, TNFR:Fc may be used to treat psoriasis in combination with topical steroids, systemic steroids, antagonists of inflammatory cytokines, antibodies against T cell surface proteins, anthralin, coal tar, vitamin D3 and its analogs (including 1,25-dihydroxy vitamin D3 and calcipotriene), topical retinoids, oral retinoids (including but not limited to etretinate, acitretin and isotretinoin), topical salicylic acid, methotrexate, cyclosporine, hydroxyurea and sulfasalazine. In addition, TNFR:Fc may be administered to treat psoriasis in combination with one or more of the following compounds; minocycline; misoprostol; oral collagen; 6-mercaptopurine; nitrogen mustard; gabapentin; bromocriptine; somatostatin; peptide T; anti-CD4 monoclonal antibody; fumaric acid; polyunsaturated ethyl ester lipids; zinc; and other drugs that may be used to treat psoriasis. TNFR:Fc may also be used to treat psoriasis in combination with the use of various oils, including fish oils, nut oils and vegetable oils; aloe vera; jojoba; Dead Sea salts; capsaicin; milk thistle; witch hazel; moisturizers; and Epsom salts. In addition, psoriasis may be treated with compositions containing TNFR:Fc in combination with the following therapies: plasmapheresis; phototherapy with ultraviolet light B; psoralen combined with ultraviolet light A (PUVA); and sunbathing.

For determining the sufficiency of treatment when treating ordinary psoriasis in accord with the invention, the TNFR:Fc (or other TNFα inhibitor) is administered in an amount and for a time sufficient to induce an improvement in an indicator such as psoriasis area and severity index (PASI) or an improvement in Target Lesion Assessment score, which is an index for assessing the severity of individual skin lesions. In one embodiment, the treatment is regarded as sufficient when the patient exhibits an at least 50% improvement in his or her PASI score, and in another embodiment, when the patient exhibits an at least 75% improvement in PASI score. The sufficiency of treatment for psoriasis may also be determined by evaluating individual psoriatic lesions for improvement in severity (Psoriasis Target Lesion Assessment Score), and continuing treatment until an improvement is noted according to this scoring system. This scoring system involves determining for an individual lesion whether improvement has occurred in plaque elevation, amount and degree of scaling or degree of erythema, and target lesion response to treatment, each of which is separately scored. Psoriasis Target Lesion Assessment Score is determined by adding together the separate scores for all four of the aforementioned indicia.

In addition to human patients, inhibitors of TNFα are useful in the treatment of autoimmune and inflammatory conditions in non-human animals, such as pets (dogs, cats, birds, primates, etc.), domestic farm animals (horses cattle, sheep, pigs, birds, etc.), or any animal that suffers from a TNFα-mediated inflammatory or arthritic condition. In such instances, an appropriate dose may be determined according to the animal's body weight. For example, a dose of 0.2-1 mg/kg may be used. Alternatively, the dose is determined according to the animal's surface area, an exemplary dose ranging from 0.1-20 mg/m$^2$, or more preferably, from 5-12 mg/m$^2$. For small animals, such as dogs or cats, a suitable dose is 0.4 mg/kg. In a preferred embodiment, TNFR:Fc (preferably constructed from genes derived from the same species as the patient), or another soluble TNFR mimic, is administered by injection or other suitable route one or more times per week until the animal's condition is improved, or it may be administered indefinitely.

Example

Evaluation of TNFR:Fc in Patients with Psoriatic Arthritis

Sixty patients with active psoriatic arthritis (PsA) were enrolled in a Phase II double-blind, randomized, placebo controlled study to determine whether the subcutaneous biweekly administration of etanercept (recombinant TNFR:Fc) was safe in this patient population and whether efficacy could be documented for both the arthritic and psoriatic aspects of this disease.

In this study, a flat dose of 25 mg of TNFR:Fc was injected subcutaneously two times a week. After 12 weeks, patients who completed the study were eligible for continuation into a 24 week open-label extension of the study, with assessments made at weeks 16, 36 and 30 days post-study. All patients participating in the study extension received etanercept, including those patients who had received placebo during the blinded portion of the study.

In order to qualify for enrollment, subjects had to have at least one of the following forms of PsA: 1) DIP involvement; 2) polyarticular arthritis, absence of rheumatoid nodules and presence of psoriasis; 3) arthritis mutilans; 4) asymmetric peripheral arthritis; or 5) ankylosing spondylitis-like PsA. Subjects furthermore had to exhibit three or more swollen joints and three or more tender or painful joints at the time of enrollment, and to have exhibited an inadequate response to NSAID therapy. Subjects who were on other medications, including methotrexate, NSAIDs or oral corticosteroids were permitted to continue these other treatments at the same dose so long as the investigator considered these other treatments to inadequately control the patient's disease. Methotrexate was concurrently taken by 47% of the etanercept group, and 47% of the placebo group, NSAIDs were concurrently taken by 67% of the etanercept and 77% of the placebos and oral corticosteroids by 40% of the etanercept and 20% of the placebo patients. Pain medications, including acetaminophen, codeine, propoxyphene napsylate, oxycodone hydrochloride, hydrocodone bitartrate and tramadol, also were permitted during the study, as well as the use of topical tar compounds.

To qualify as having PsA, patients had to have experienced at least one psoriatic lesion of the skin or nails. Patients were evaluated at baseline (day 1 of treatment) as follows: 1) complete joint assessment; 2) psoriasis assessment; 3) duration of morning stiffness; 4) health assessment (quality of life) questionnaire, visual analog scale (HAQ/VAS); 5) patient global assessment; 6) erythrocyte sedimentation rate (ESR, Westergren); 7) C-reactive protein (CRP); and 8) urinalysis. At weeks 4 and 8, patients were evaluated as follows: 1) complete joint assessment; 2) psoriasis assessment; 3) duration of morning stiffness; 4) HAQ/VAS; 5) patient global assessment. At the end of 12 weeks, subjects were evaluated as follows: 1) complete joint assessment; 2) psoriasis assessment; 3) focused physical exam; 4) duration of morning stiffness; 5) HAQ/VAS; 6) patient global assessment; 6) hematology profile; 7) chemistry profile; 8) ESR; 9) CRP; 10) urinalysis; 11) serum tested for antibody to TNFR:Fc. Only those patients whose psoriasis was stable and covered $\geq 3\%$ of body area were evaluated for psoriasis response during this trial, although patients whose psoriasis was inactive or covered less area were permitted to enroll.

A primary endpoint for clinical improvement or worsening of PsA was the Psoriatic Arthritis Response score, which is a composite score based on the following four measures: 1) patient self-assessment; 2) physician assessment; 3) joint pain or tenderness; 4) joint swelling. Both self- and physician assessments, i.e., overall assessment of disease status, were measured according to a five point Likert scale, in which a patient was considered as "improved" if his or her score decreased by one category, or as "worse" if his or her score increased by one category. Joint pain or tenderness was measured on a 5-point scale, wherein 1=none and 5=severe (withdrawal on examination). Joint swelling was evaluated on a 4-point scale in which 1=none; 2=mild (detectable synovial thickening without loss of bony contour); 3=moderate (loss of distinctness of bony contours); and 4=severe (bulging synovial proliferation with cystic characteristics). For this last measure, a decrease in swelling of $\geq 30\%$ was scored as an "improvement," and an increase in swelling of $\geq 30\%$ was scored as a "worsening." Patients were classified as "improved" under the Psoriatic Arthritis Response scoring system if they exhibited an improvement in at least two of the four measures described above, provided that one of the improved areas was joint pain or joint tenderness, and where there was no worsening in any of the four measures.

In addition, a secondary endpoint used for assessing psoriatic arthritis was a modified version of the American College of Rheumatology Preliminary Definition of Improvement in Rheumatoid Arthritis (modified ACR 20 response) (Felson et al., 1995). To qualify as "improved" according to this measure, a patient must have exhibited $\geq 20\%$ improvement in both tender joint count (78 joints assessed) and swollen joint count (76 joints assessed), and also must have shown an improvement in three of the following five: 1) subject pain assessment; 2) subject global assessment; 3) physician global assessment; 4) subject self-assessed disability; 5) acute-phase reactant (Westergreen erythrocyte sedimentation rate or C-reactive protein level). The joint count was done by scoring several different aspects of tenderness, such as pressure and joint manipulation on physical examination, wherein each joint was scored as "tender" or "nontender." Similarly, each joint is scored after physical examination as "swollen" or "not swollen." The subject's pain assessment was based on a horizontal visual analog scale (usually 10 cm) or Likert scale. The subject's and physician's global assessments of the subject's current disease status was based on an anchored horizontal visual analog scale (usually 10 cm), or Likert scale response. The subject's self-assessment of disability was based on any of the following measures, all of which have been validated in RA trials: Arthritis Impact Measurement Scale (AIMS); Health Assessment Questionnaire; the Quality (or Index) of Well Being Scale; the McMaster Health Inventory Questionnaire (MHIQ); and the McMaster-Toronto Arthritis patient preference questionnaire (MACTAR).

A primary endpoint used to assess the psoriatic aspects of PsA was the standard psoriasis area and severity index (PASI) (Fredriksson and Petersson, *Dermatologica* 157:238-244, 1978). For this study, a positive treatment response was defined as an at least 50% or an at least 75% improvement in a patient's PASI score. For assessing area and severity, the body is divided into four regions: head (10%); trunk (30%); upper extremities (20%); and lower extremities (40%). Each quadrant also was scored for the severity of erythema (E), infiltration (I) and desquamation (D), using a four point scale, in which 0=no symptoms present; 1=slight symptoms; 2=moderate symptoms; 3=striking symptoms; 4=exceptionally striking symptoms. Using a 6-point scale, each region was scored also for the percent of total area that was involved in the psoriatic manifestations of the disease, wherein 0=no involvement; 1=<10% involvement; 2=10-<30% involvement; 3=30-<50% involvement; 4=50-<70% involvement; 5=70-<90% involvement; 6=90-100% involvement. PASI scores were calculated according to the formula given below, in which E=severity score for erythema, I=severity score for infiltration, D=severity score for desquamation and A=total area involved. In this formula, the letters "h," "t," "u" and "l" represent, respectively, the scores in each of the four body regions, i.e., head, trunk, upper extremities and lower extremities. The PASI score varies in steps of 0.1 units from 0.0 (no psoriatic lesions at all) to 72.0 (complete erythroderma of the severest possible degree).

$$PASI=0.1(Eh+Ih+Dh)Ah+0.3(Et+It+Dt)At+0.2(Eu+Iu+Du)Au+0.4(El+Il+Dl)Al$$

A secondary endpoint used for the psoriatic aspect of psoriatic arthritis was the Target Lesion Assessment Score. This score was determined for a single target lesion that was selected to be monitored throughout the trial. This measurement is a composite of four different evaluations: 1) plaque evaluation; 2) scaling; 3) erythrema; and 4) target lesion response to treatment. The following scale was used for the plaque elevation: 0=none (no evidence of plaque above normal skin level); 1=mild (slight but definite elevation above normal skin level); 2=moderate (moderate elevation with rounded or sloped edges to plaque); 3=severe (hard, marked elevation with sharp edges to plaque); 4=very severe (very marked elevation with very hard sharp edges to plaque). For the scaling assessment: 0=none (no scaling on the lesion); 1=mild (mainly fine scales, with some of the lesion at least partially covered); 2=moderate (somewhat coarser scales, most of the lesion at least partially covered); 3=severe (coarse, thick scales, virtually all the lesion covered, rough surface); 4=very severe (very coarse thick scales, all the lesions covered, very rough surface). For the erythema evaluation: 0=none (no erythema); 1=mild (light red coloration); 2=moderate (red coloration); 3=severe (very red coloration); 4=very severe (extreme red coloration). For target lesion response to treatment score: 0=completely cleared; 1=almost cleared (~90% improvement); 2=marked response (~75% improvement); 3=moderate response (~50% improvement); 4=slight response (~25% improvement); 5=condition unchanged; 6=condition worsened. The patient's Target Lesion Assessment Score was determined by summing the plaque, scaling, erythema and target lesion response scores for the monitored lesion. If the monitored lesion worsened, the percentage change from baseline was recorded as a negative number.

Treatment and placebo groups were compared in accord with the measurements described above, as well as for demographic and background characteristics; premature discontinuation rate; pain medication requirements; toxicities; serious adverse events; side effects reported by patients; number of weeks on drug until subjects met criteria for improvement, and response according to PsA subtype. Results were analyzed using standard statistical methods.

Dosing Regimen

Recombinant human TNFR:Fc (etanercept) from Immunex Corporation was used in this study. The gene fragments encoding the etanercept polypeptides were expressed in a Chinese hamster ovary (CHO) expression vector.

TNFR:Fc was supplied as a sterile lyophilized powder containing 10 mg or 25 mg TNFR:Fc; 40 mg mannitol, USP; 10 mg sucrose, NF; and 1.2 mg tromethamine (TRIS), USP per vial. Patients received either a dose of 25 mg of etanercept or a placebo. Vials of etanercept or identically-appearing placebo were reconstituted by aseptic injection of 1.0 mL Bacteriostatic Water for Injection, USP, (containing 0.9% benzyl alcohol), and was not filtered during preparation or prior to administration. If storage was required, the reconstituted solutions were stored at 2-8° C. (36-46° F.) in the original vial or in a plastic syringe for a period of no longer than 28 days. Dose was not changed during the study. Study drug was given twice weekly at approximately the same time of day.

Results

Study drug was well tolerated in all patients, and adverse events were consistent with this population and were equally distributed among both treatment groups. As illustrated in Tables 1-4, etanercept induced a significant improvement as compared with the placebo group in Psoriatic Arthritis Response (Table 1), ACR20 (Table 2), ACR50 (Table 3), PASI score, 50% improvement (Table 4), PASI score, 75% improvement (Table 5) and improvement in Target Lesion Assessment Score (Table 6). The fractions shown in Tables 1-5 represent numbers of patients. For example, the first entry in Table 1, which is "4/30," indicates that 4 of 30 patients in the placebo group scored as "improved" according to the Psoriatic Arthritis Response measurements. The tables include P-values for the differences between the two study groups, the groups being labeled as "PLACEBO" and "TNFR:Fc." All of the tables include data calculated after the first four weeks of the open label extension portion of the study ("EXTENSION"), during which all of the patients in both study groups received etanercept.

Table 1 shows the number of patients in each treatment group who scored as "improved" according to the Psoriatic Arthritis Response scoring system described above. By four weeks, there was a highly significant difference between etanercept and placebo groups. Moreover, after being switched to etanercept during the extension, those patients who had received placebo during the blinded portion of the study were seen to exhibit an improvement over baseline (Table 1, Placebo, EXTENSION). These results indicate that etanercept acts rapidly to alleviate many aspects of psoriatic arthritis.

TABLE 1

Psoriatic Arthritis Response

|  | Placebo | TNFR:Fc | P-value |
| --- | --- | --- | --- |
| 4 weeks | 4/30 (13%) | 23/30 (77%) | 0.000 |
| 8 weeks | 7/30 (23%) | 25/30 (83%) | 0.000 |
| 12 weeks | 6/30 (20%) | 26/30 (87%) | 0.000 |
| EXTENSION | 17/23 (74%) | 21/25 (84%) | 0.356 |

Tables 2 and 3, respectively, illustrate the study results for the ACR20 and ACR50 endpoints. For either measure, a significant difference between etanercept and placebo groups was observed at all three time points during the blinded portion of the study. Given the differences between test and placebo groups after only four weeks of treatment (P=0.000 for ACR20 and P=0.011 for ACR50), these data suggest that notable improvement in ACR scores occurred within the etanercept group very soon after treatment was initiated, possibly after a single dose of etanercept. During the 4 week extension period, during which all of the patients received etanercept, a striking improvement in both ACR20 and ACR50 was seen in those patients who had received placebo during the first 12 weeks (Tables 2 and 3).

TABLE 2

ACR20 Response

|  | Placebo | TNFR:Fc | P-value |
| --- | --- | --- | --- |
| 4 weeks | 1/30 (3%) | 18/30 (60%) | 0.000 |
| 8 weeks | 3/30 (10%) | 19/30 (63%) | 0.000 |
| 12 weeks | 4/30 (13%) | 22/30 (73%) | 0.000 |
| EXTENSION | 11/23 (48%) | 18/25 (72%) | 0.093 |

TABLE 3

ACR50 Response

|  | Placebo | TNFR:Fc | P-value |
| --- | --- | --- | --- |
| 4 weeks | 0/30 (0%) | 6/30 (20%) | 0.011 |
| 8 weeks | 1/30 (3%) | 11/30 (37%) | 0.001 |
| 12 weeks | 1/30 (3%) | 15/30 (50%) | 0.000 |
| EXTENSION | 7/23 (30%) | 11/25 (44%) | 0.316 |

The results of the psoriasis evaluations are presented in Tables 4-6. Tables 4 and 5, respectively, present the numbers and percentages of patients in each group who exhibited a 50% or 75% improvement in PASI score, while Table 6 presents Target Lesion Assessment scores, these latter being denoted as percent improvement over baseline. The data in Tables 4-6 clearly indicate that etanercept induced an improvement in psoriasis for a large percentage of the patients who received it. When single lesions were evaluated (Table 6), the improvement in psoriasis was even more apparent than when PASI scores were used (Tables 4 and 5). It is notable also that, for either PASI scores (Tables 4 and 5) or Psoriasis Target Lesion Assessment Score (Table 6), the scores of the placebo group improved after these patients were switched to etanercept during the extension.

Though not shown in Table 6, Target Lesion Assessment Scores for patients who were concurrently receiving methotrexate (14 of the 30 patients in the etanercept group, and 14 patients in the placebo group) were compared with the scores of those patients who did not take methotrexate. Little difference in this index was noted between the patients who received methotrexate and those who did not receive it.

TABLE 4

PASI Score - 50% Improvement

|  | Placebo | TNFR:Fc | P-value |
| --- | --- | --- | --- |
| 4 weeks | 0/19 (0%) | 4/19 (21%) | 0.037 |
| 8 weeks | 1/19 (5%) | 7/19 (37%) | 0.019 |
| 12 weeks | 4/19 (21%) | 8/19 (42%) | 0.165 |
| EXTENSION | 6/16 (38%) | 6/15 (40%) | 0.856 |

TABLE 5

PASI Response Rate 75% Improvement

|  | Placebo | TNFR:Fc | P-value |
|---|---|---|---|
| 4 weeks | 0/19 (0%) | 1/19 (5%) | 0.264 |
| 8 weeks | 0/19 (0%) | 2/19 (11%) | 0.153 |
| 12 weeks | 0/19 (0%) | 4/19 (21%) | 0.037 |
| EXTENSION | 1/16 (6%) | 4/15 (27%) | 0.113 |

TABLE 6

Psoriasis Target Lesion Assessment
(Percent Improvement or Worsening Compared with Baseline)

|  |  | Placebo | TNFR:Fc | P-value |
|---|---|---|---|---|
| 4 weeks | Mean (SD) | 2.7 (27.6) | 21.2 (35.2) | 0.120 |
|  | Median | 0.0 | 14.3 |  |
|  | MIN--MAX | −50.0-50.0 | −33.3-100.0 |  |
|  | N | 19 | 19 |  |
| 8 weeks | Mean (SD) | −7.5 (25.3) | 28.5 (34.1) | 0.003 |
|  | Median | 0.0 | 29.2 |  |
|  | MIN--MAX | −50.0-20.0 | −33.3-100.0 |  |
|  | N | 17 | 18 |  |
| 12 weeks | Mean (SD) | 9.5 (23.2) | 45.7 (31.6) | 0.001 |
|  | Median | 0.0 | 50.0 |  |
|  | MIN--MAX | −25.0-50.0 | −16.7-100.0 |  |
|  | N | 16 | 19 |  |
| EXTENSION | Mean (SD) | 28.9 (41.2) | 47.1 (35.8) | 0.263 |
|  | Median | 36.7 | 50.0 |  |
|  | MIN--MAX | −100.0-66.7 | −33.3-100.0 |  |
|  | N | 16 | 15 |  |

What is claimed is:

1. A method for treating a patient having psoriasis comprising administering to the patient a therapeutically effective dose of TNFR:Fc, wherein the patient attains at least fifty percent improvement in PASI score.

2. The method of claim 1, wherein the dose of TNFR:Fc administered is either 50 mg once per week or 25 mg twice per week.

3. The method of claim 1, wherein the dose of TNFR:Fc administered is 50 mg twice per week.

4. The method of claim 1, wherein the TNFR:Fc is administered by subcutaneous injection.

5. The method of claim 1, wherein
  (a) a dose of 50 mg of TNFR:Fc is administered two times per week for at least two months and then
  (b) TNFR:Fc is administered at a reduced dose or at a reduced frequency.

6. The method of claim 5, wherein the administration of (b) is at a dose 25 mg of TNFR:Fc twice per week.

7. The method of claim 5, wherein the administration of (b) is at a dose of 50 mg once per week.

8. The method of claim 5, wherein the TNFR:Fc is administered by subcutaneous injection.

9. The method of claim 1, wherein the patient exhibits at least seventy five percent improvement in PASI score after three months of treatment.

10. The method of claim 1, wherein a corticosteroid is administered concurrently.

11. The method of claim 1, wherein methotrexate is administered concurrently.

12. A method for treating a patient having psoriasis and psoriatic arthritis comprising administering to the patient a therapeutically effective dose of TNFR:Fc, wherein the patient attains at least fifty percent improvement in PASI score.

13. The method of claim 12, wherein the dose of TNFR:Fc administered is either 50 mg once per week or 25 mg twice per week.

14. The method of claim 12, wherein a corticosteroid is administered concurrently.

15. The method of claim 12, wherein methotrexate is administered concurrently.

16. A method for treating a patient having psoriasis comprising
  (a) administering to the patient TNFR:Fc subcutaneously at a dose of 50 mg twice per week for at least two months and then
  (b) administering TNFR:Fc subcutaneously at a dose of 50 mg once per week or at a dose of 25 mg twice per week.

17. The method of claim 1, wherein cyclosporine is administered concurrently.

18. The method of claim 1, wherein acitretin is administered concurrently.

19. The method of claim 1, wherein ultraviolet light B phototherapy or psoralen combined with ultraviolet light A (PUVA) phototherapy is administered concurrently.

20. The method of claim 16, wherein the patient attains at least fifty percent improvement in PASI score.

* * * * *